US006127571A

United States Patent [19]

Mulvaney, III

[11] Patent Number: 6,127,571

[45] Date of Patent: Oct. 3, 2000

[54] CONTROLLED REACTANT INJECTION WITH PERMEABLE PLATES

[75] Inventor: Robert C. Mulvaney, III, Arlington Heights, Ill.

[73] Assignee: UOP LLC, Des Plaines, Ill.

[21] Appl. No.: 08/999,877

[22] Filed: Nov. 11, 1997

[51] Int. Cl.[7] .................................. C07C 309/00

[52] U.S. Cl. .................................. 562/98; 562/99

[58] Field of Search .................................. 562/98, 99

[56] References Cited

U.S. PATENT DOCUMENTS

| | | | |
|---|---|---|---|
| 2,088,027 | 7/1937 | Law et al. | 562/99 |
| 2,691,040 | 10/1954 | Bloch et al. | 562/99 |
| 2,923,728 | 2/1960 | Falk et al. | 562/98 |
| 5,193,611 | 3/1993 | Hesselgreaves | 165/165 |
| 5,316,628 | 5/1994 | Collin et al. | 203/72 |

*Primary Examiner*—Paul J. Killos
*Assistant Examiner*—Taylor V. Oh
*Attorney, Agent, or Firm*—John G. Tolomei

[57] ABSTRACT

An arrangement for a fluid distributor-contactor type reactor uses perforated plates to circulate two reactants in alternate channels defined by spaces between parallel stacked plates to perform controlled distribution and mixing simultaneously with optional indirect heat transfer. One reactant enters one set of channels that serve as reaction channels. A set of second channels interleaved with the reaction channels serve as distribution channels that also provide a heat exchange function. Finely dispersed openings in the perforated plates distribute the reactant at low concentration from the distribution channels into the reaction channels. Dispersal of the reactant through the perforations will enhance the turbulence that is primarily introduced by the corrugated plates to insure good mixing of the reactants in the reaction channels. The pattern and size of the holes on the perforated plates may be varied as desired to disperse a carefully controlled amount of fluid across the plates over a large surface area. By maintaining a low addition rate of injected fluid reactant over the contact area, the concentration of the added reactant in the reaction channels may be kept as low as desired. The plates are preferably corrugated to introduce increased turbulence for promoting better distribution and dispersion of the fluids as one fluid is injected across the perforations. The corrugation angles can also be varied to suit the fluid flow properties of the fluid reactant and in particular varied over the height of the contacting zone to vary fluid residence time over different parts of the plates.

12 Claims, 3 Drawing Sheets

B
32
10
12
22
B
A
C
B
A
22
28
30
B 24
54
34
C
36
50
52
18
38

CONTROLLED REACTANT INJECTION WITH PERMEABLE PLATES

FIELD OF THE INVENTION

This invention relates generally to the interaction of the dispersal and mixing of one reactant stream into another. More specifically this invention relates to the use of plate structures for distribution, contacting and mixing of reactants.

BACKGROUND OF THE INVENTION

Certain chemical reactions are highly sensitive to the contacting conditions under which the reactants are brought together. Contacting conditions that can have a profound effect on the production of products in some reactions include physiochemical conditions such as reaction time, reagent concentration, reagent dispersion and temperature conditions. An example of a highly sensitive process of this type is the sulfonation of various compounds with a sulfonating agent. The initially formed sulfonates indicate a relatively high thermodynamic instability. It is well known that mild sulfonation conditions including short reaction times and low concentration gradients yield different products when compared to more drastic operating conditions.

A common method of controlling the contact between reactants in a reaction that is highly sensitive to process conditions is by the use of a thin film or falling film reaction zone. Falling film evaporators and reactors are well known in the art and are readily available commercially. Falling film evaporators pass a thin film of a liquid stream down one side of a heat exchange surface in indirect heat exchange with a heating medium that contacts an opposite side of the heat exchange surface and causes an at least partial evaporation of the falling liquid. Falling film reactors comprise a plurality of tubes or plates over which a thin film of one reactant is dispersed for countercurrent or cocurrent contact with a gaseous reactant stream. In the case of evaporation or reaction laminar flow layers in the thin film can inhibit heat transfer and diffusion of vapor.

One of the most well known falling film reactor arrangements is for the continuous sulfonation or sulfation of fluid state organic substances by reaction with sulfur trioxide (sulfuric anhydride) ($SO_3$). In traditional falling film arrangements, the $SO_3$ or other reactant is kept in a gaseous state. The reaction of the $SO_3$ with the organic substances is strongly exothermic throughout the reaction which occurs rapidly or in many cases goes nearly instantaneously to completion. The gaseous $SO_3$ is normally diluted with air or other inert gases to a reduced concentration of 4–15 wt % which attenuates the severity of the reaction. The provision of cooling to the falling film contact surfaces also avoids the generation of temperature peaks from the highly exothermic reaction.

U.S. Pat. No. 3,925,441 issued to Toyoda et al. describes the use of flat plates for falling film sulfonation.

U.S. Pat. No. 5,445,801 to Pisoni describes a tube arrangement for falling film sulfonation that provides improved liquid distribution and accommodates expansion of the tubes.

U.S. Pat. No. 4,059,620 issued to Johnson describes the advantages of maintaining a desired heat exchange profile during the sulfonation of organic compounds with sulfur trioxide.

The sulfonation or reaction of other organic compounds can cause extensive side reactions. Side reactions are best minimized by a uniform distribution of the falling liquid with gaseous reactants over the contact surfaces. Perhaps more important is the need to keep the sulfonating compound in relatively low concentration. Systems for controlling the distribution of liquid into tubes or plate arrangements for falling film reactors include: weir and dam systems and slit or orifice arrangements that can be mechanically adjusted in various ways. Nevertheless, minor irregularities in the delivery systems to the top of the falling film apparatus can result in substantial flow variations with the attendant drawback of side reaction production. In addition to the problems associated with uniform delivery to a falling film contact surface, variations in the surface also create flow irregularities that can lead to non-uniform contacting and promote side reaction production.

The systems that use a gaseous phase reactant to contact the wetted walls of the falling film reactor also have the disadvantage or requiring a large circulation of gas in addition to the circulation of the liquid phase material down the walls of the reactor and the circulation of a cooling fluid. Care must be taken to control the concentration of the gaseous reactant in the gas phase. As a result the gas phase reactant is typically diluted with another gas to maintain a low reactant concentration and avoid unwanted by-product formation. For example in the sulfonation of aromatic hydrocarbons, a film of aromatic hydrocarbon is passed down the walls of channels through which an air stream containing dilute SO3 circulates. Supplying the air stream requires continual drying of large quantity of air if the air passes once through the channels. Recirculation of the air ordinarily necessitates purification to prevent product re-entrainment which will cause by-product formation.

The use of a permeable wall to introduce reagents into reaction zones is disclosed in U.S. Pat. No. 3,375,288. It is known to carry out a sulfonation reaction with liquid phase reagents in a reaction zone that has fluid permeable walls. An article attributed to the Stanford Research Institute and published in the June 1996 issue of Chemical Engineering Magazine and U.S. Pat. No. 5,503,240 discloses the passing of a sulfonation agent through permeable tubes that are surrounded by the sulfonation substrate. The tubes have a low permeability that maintains the sulfonating agent in low concentration. The tubes contain a packing of particulate material to provide the required good mixing of the sulfonating agent that permeates the tube wall.

A reactor system is sought that will eliminate the need for diluent gas addition or recirculation, reduce boundary layer limitations in the dispersion of a reagent in low concentrations in a liquid contactors, overcome any initial maldistribution of liquid reactants in a liquid phase contactor, avoid the need for internal packing and facilitate the control of reaction temperature by promoting indirect heat transfer.

SUMMARY OF THE INVENTION

Accordingly, an object of this invention is to provide an apparatus and process for a fluid contactor that continually redistributes reactants.

Another object of this invention is to provide a fluid reactant contactor that facilitates good distribution and dispersion while promoting thorough mixing of the dispersed compound into a reagent.

A yet further object of this invention is to provide good distribution and dispersion of reaction fluids while simultaneously facilitating indirect heat exchange.

These and other objectives are achieved by an arrangement for a fluid distributor contactor type reactor that uses plates containing permeable or perforated portions. The arrangement circulates the two reactants in alternate channels defined by spaces between parallel stacked plates. One reactant enters one set of channels that serve as reaction channels. A set of second channels, interleaved with the reaction channels, serve as distribution channels that can also provide a heat exchange function. Finely dispersed openings or permeation sites in the perforated plates distribute one reactant at low concentration from the distribution channels into the reaction channels. Dispersal of the reactant through the plate will introduce turbulence and promote good mixing of the reactants in the reaction channels. The pattern and size of the holes or permeable sections on the perforated plates may be varied as desired to disperse a carefully controlled amount of fluid across the plates over a large surface area. By maintaining a low addition rate of injected fluid reactant over the contact area, the concentration of the added reactant in the reaction channels may be kept as low as desired. Pressure drop across the perforated plate may be controlled to attain the desired degree of reactant penetration into the reaction channels. In liquid phase systems the addition of the reactant directly into the reaction channels eliminates the gas medium and any need for the associated recycle, separation or drying that were part of falling film contacting.

It is also useful to provide the perforated plates with a form or projections that increase the turbulence in the reaction channels. Such forms can include pins, rods or tabs extending outward from the plates to mildly agitate the flow through the reaction channels. Such flow agitation should be kept below a level that will cause substantial variation in the residence time of reactant through the reaction channels. A preferred plate form for introducing turbulence use corrugated plates that are stacked next to or in close proximity to each other to create the reactant and distribution flow channels.

The distribution channels that supply the liquid reactant to the perforations can also provide the passageways for indirect heat exchange of the reactant and product fluid in the reaction channels with the fluid in the distribution channels on the opposite side of the plates. A large excess volume of the second reactant normally circulates through the heat exchange channels to provide sufficient heating or cooling with only a small amount of the fluid reactant passing through the perforations for reaction in the reaction channels. The reactant is preferably circulated through the distribution channels at a much higher circulation rate than the dispersal rate of fluid across the reaction channels. Thus the reactant circulates at a high rate in the distribution channels as an optional indirect heat transfer fluid. Preferably the perforated plates will have a shape or form that promotes a high degree of heat transfer between the distribution and the reaction channels. Thin wall, relatively flat plates provide the best heat transfer characteristics. Again turbulence introducing forms or structures for the perforated plates are again beneficial for the heat transfer as well as the mixing functions. Corrugated plates are the preferred turbulence introducing form for both heat transfer and mixing. The injection of the reactant fluid from the heat exchange channels when performed with sufficient pressure drop provides velocity that also aids in creating turbulence.

The corrugations on the preferred form of the plates can be varied to suit the fluid flow properties of the fluid and in particular may be varied over the height of the contacting zone to vary fluid residence time and turbulence over different parts of the plates. The corrugated plates may be spaced apart to increase the flowing volume in either the reactant or distribution channels but preferably make contact with each other to provide structural stability. Turbulence introduced by the corrugated plates will again facilitate indirect heat transfer between the reactants in the distribution and reaction channels. In this manner the corrugated plate arrangement provides advantages for the dispersion, the contacting, the mixing and the heating or cooling of fluids in the reaction channels and in and between the reaction and distribution channels.

Accordingly, in a broad process embodiment this invention is a process for the reaction of a fluid stream by the controlled addition of a fluid reactant. The process passes a first stream comprising a reactive fluid into a plurality of reaction channels defined by a first side of a plurality of stacked plates. A second stream comprising a reactant fluid circulates through a plurality of distribution channels defined by a second side of the plates to supply a reactant fluid and optionally to provide indirect heat exchange with the reactive fluid. Permeable portions distributed over the surface of the plates to control the contact of the reactant fluid with the reactive fluid distribute a portion of the reactant fluid into the reaction channels. The process recovers a reaction product from the reaction channels.

More specific process embodiments deal with the manner of distributing fluid and the specific fluid components and reactions. One such reaction is the sulfonation of a substrate with sulfur trioxide. Another reaction could be the contacting of a subcooled ethylene oxide containing liquid with an organic material to perform ethoxylation.

In an apparatus embodiment this invention is a reactor for the controlled distribution of reactants. The reactor includes a plurality of contacting plates, containing perforation or permeable sections, stacked adjacent to one another to define reaction channels between the first sides of adjacent plates. Means are provided for passing a first fluid into the reaction channels. A distribution channel located between each reaction channel and defined by the second side of the plates distribute a second fluid through the plates and optionally circulate the second fluid as an indirect heat exchange medium. Means are provided for supplying the second fluid to the distribution channels and for collecting a fluid stream containing a reaction product from the reaction channels.

This invention may use any type of plate to define the alternate reaction and distribution channels. Preferred plates for this invention are those that will enhance the distribution of the fluid reactant that is injected through the plates into contact with the other liquid stream. The plate surface can enhance the intermixing of components by introducing additional turbulence to the surface of the plate defining the reaction channels. The turbulence should be enough to intermix the different fluids but not so great as to cause extensive backmixing of the fluids that can lead to non-uniform contacting and by-product generation. Corrugated plates with corrugations extending transverse to the direction of fluid circulation can be particularly beneficial in this regard.

In particular, corrugations on the contacting plates can be varied to suit the particular characteristics of the process and fluids employed. For low surface tension and low viscosity fluids, a relatively horizontal and shallow pitched corrugation is most beneficially employed. A slight downward pitch may be provided on the horizontal corrugations to provide a transverse movement when a liquid phase is present. The corrugation sections are preferably in a herring bone pattern so that the fluid flows back and forth in a horizontal direction across the reactor as it moves downwardly over the reactor thereby increasing the redistribution and uniformity of the flow. The number and height of corrugation rows can be varied in order to increase the dispersion of the fluids passing along the corrugations. In the case of liquids, as the viscosity of the liquid reactants increases, the slope of the corrugations and depth of the corrugations may be increased to provide additional redistribution and turbulence.

Controlled addition of the fluid reactant into the reaction channel is accomplished by distributing a portion of the fluid from the distribution channels across the plates through permeable sites that extend over a large area of the plates. When the contactor is used to provide an indirect heat exchange function, a relatively small amount of the fluid circulating in the distribution channels, usually less than 10% of the total circulating fluid, will normally pass through the permeable portions of the plate into contact with the fluid in the reaction channels films. More typically the amount of fluid passing through the plates will be less than 5% of the total circulating fluid entering the distribution/heat exchange channels.

Any type of structure may be used to provide the permeable sections of the plates. In simplest form the plates will contain a widely dispersed array of relatively fine perforations. The size and number of the perforations will of course depend on the fluid properties at the desired operating conditions. Fluid phase will typically be the most important fluid property. The invention can use all liquid phase fluids all gas phase fluids or may inject a liquid phase into a gas phase or a gas phase into a liquid phase. Other important fluid properties are the desired concentration of the fluid in the reaction channels and the pressure drop across the plates. In reactions such as sulfonation the perforations will ordinarily be in a size range of from 0.1 mm to 1 mm and will create about 5–10% open area across the plates. It may be desirable to decrease the density or size of perforation in the lower portions on the plates as more of the fluid in the reaction channels has been converted to product and need for additional reactant injection diminishes.

The multitude of perforations can have the added advantage of again introducing a desired degree of turbulence. Pressure drop across the plates may be regulated to further control turbulence. A low pressure drop prevents the formation of extended fluid jets. Relatively high pressure drops are generally preferred to provide additional turbulence and further enhance mixing. High pressure drops may be particularly preferred where the fluid phases differ and a large jet may be desirable to force injected reactant gas across a liquid reactive stream. High pressure drop may also atomize a reactant liquid as it mixes with a reactive gas stream. Suitable pressure drops will vary widely depending of the fluid properties and the size of the perforations.

Suitable plate elements for this invention may also have a composite construction wherein a permeable material is incorporated onto the plates between the channels over holes in the plate. The permeable material can comprise an ultra-fine screen that inhibits any jet creation as liquid passes through the plate. Exposure of the circulating liquid to a fine screen material can introduce the desired turbulence and the well dispersed area of permeable sections over the plate while the plate provides the necessary support of the screen material. Permeable membranes or other coatings across perforations would also provide a useful structure, especially for the control of gas phase flow, but are not preferred when performing simultaneous heat exchange since their insulating effects may interfere with the indirect heat transfer across the plate.

Additional details, embodiments, and arrangements of this invention are described in the following "detailed description of the invention."

DETAILED DESCRIPTION OF THE INVENTION

Figure 1:
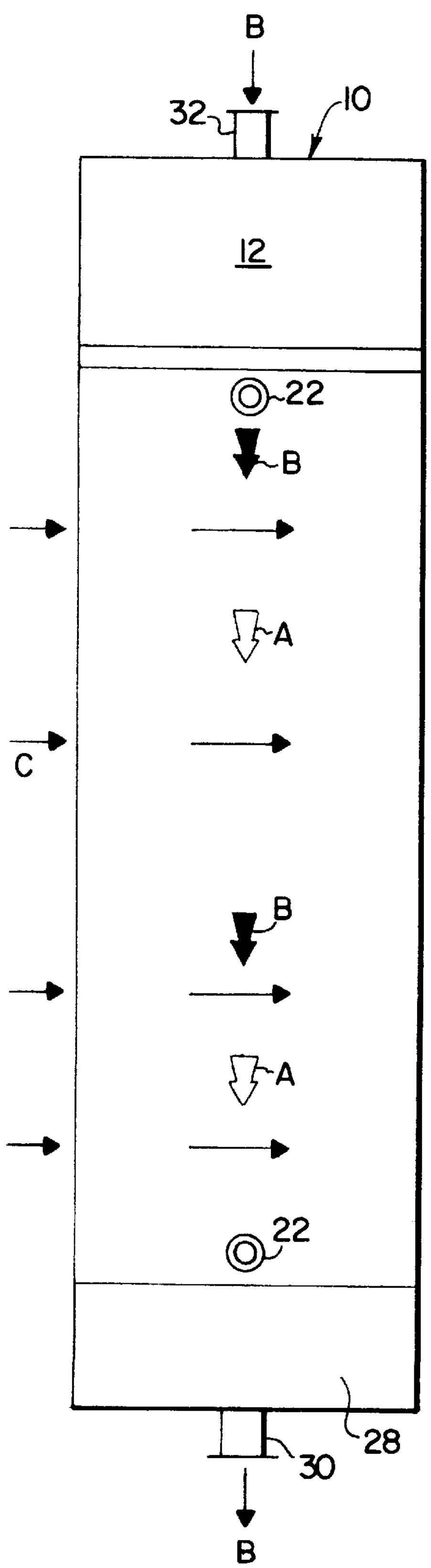
FIG. 1 is a schematic diagram showing a plate reactor of this invention and possible directions for process flow streams.

This invention is broadly applicable to any system in which a reactant fluid requires highly controlled introduction into another fluid. The contacting takes place by the circulation of the reactant in contact with a surface and the diffusion of the reactant fluid through the contact surface into contact with reactive fluid. The invention is most beneficial when the injected reactive fluid can also serve as an indirect heat exchange fluid.

The turbulence induced by the injection of the fluid into the film may be useful in the dispersion of the injected fluid throughout the fluid. As mentioned a corrugated plate may be another useful method of introducing turbulence for the distribution of the portion of the reaction and heat exchange liquid throughout the other liquid stream. The turbulence induced by the injection of the fluid as well as the optional corrugations can maintain mixing as the fluid flows to overcome laminar flow characteristics that give rise to temperature or concentration gradients. The turbulence induced by the injected fluid as well as any corrugations or turbulence inducing means will allow the dilute reaction to continue at high efficiency and with a dilute concentration of the reactive fluid over the entire height of the contacting surface.

A common example of a reaction suitable for the process and apparatus of this invention is in a sulfonation process which is meant to designate any procedure by which a sulfonic acid group with a corresponding salt or sulfonal halide is attached to a carbon atom. The sulfonation method for which this invention is most broadly suited is the treatment of an organic compound with a liquid phase sulfur trioxide. Common starting compounds for this sulfonation reaction include substrate materials such as alkyl olefins having 8–30 carbon atoms, alkyl benzenes having 8–15 carbon atoms, and aliphatic alcohols having 8–24 carbon atoms. A particularly preferred starting compound is toluene. The organic compounds enter the reaction channels in a liquid phase. Typical temperatures for substrate material in the reaction channels are in the range of 10–45° C. although actual temperatures may vary substantially with the organic material. The organic compounds may pass through the reaction channels in cross flow, countercurrent flow or cocurrent flow with respect to the flow of the reactant through the distribution channels.

The invention is particularly useful for sulfonation reactions. Suitable sulfonating agents for the reactant stream include $SO_3$, sulfuric acid ($H_sSO_4$) and oleum $H_sS_2O_7$ . $SO_3$ is the preferred sulfonating agent since it is essentially completely reacted to product and there is typically no need for downstream separation or recovery of the sulfonation reactant. Oleum and sulfuric acid on the other hand are not reacted to completion and will usually require a downstream separation stage for recovery when employed as the sulfonating agent.

The preferred $SO_3$reactant may be introduced into the reaction zone in combination with any suitable inert liquid, but is most advantageously added in a relatively pure form. One particular advantage of this invention is its suitability for introducing a relatively pure reactant stream into contact with the reactive stream. When using this invention for sulfonation, a reactive hydrocarbon stream may be sulfonated with an $SO_3$ reactant at a 98% conversion on a once through passage of the reactive stream.

Another highly beneficial use of the reactor arrangement of this invention is in its use as an ethoxylation reactor. In such reactions, the material to be ethoxilated such as an alcohol or an alkylphenol flows through the reaction channels. Ethylene oxide is circulated as a liquid in a cocurrent or countercurrent direction. Close temperature control in such reactions is desired to prevent the formation of unwanted side products. The use of the corrugations, the liquid injection and the heat exchange of this invention over a flat plate surface promotes liquid turbulence and overcomes the laminar nature of the flow which induces severe temperature and concentration gradients across the ethoxylated compounds.

Figure 2:
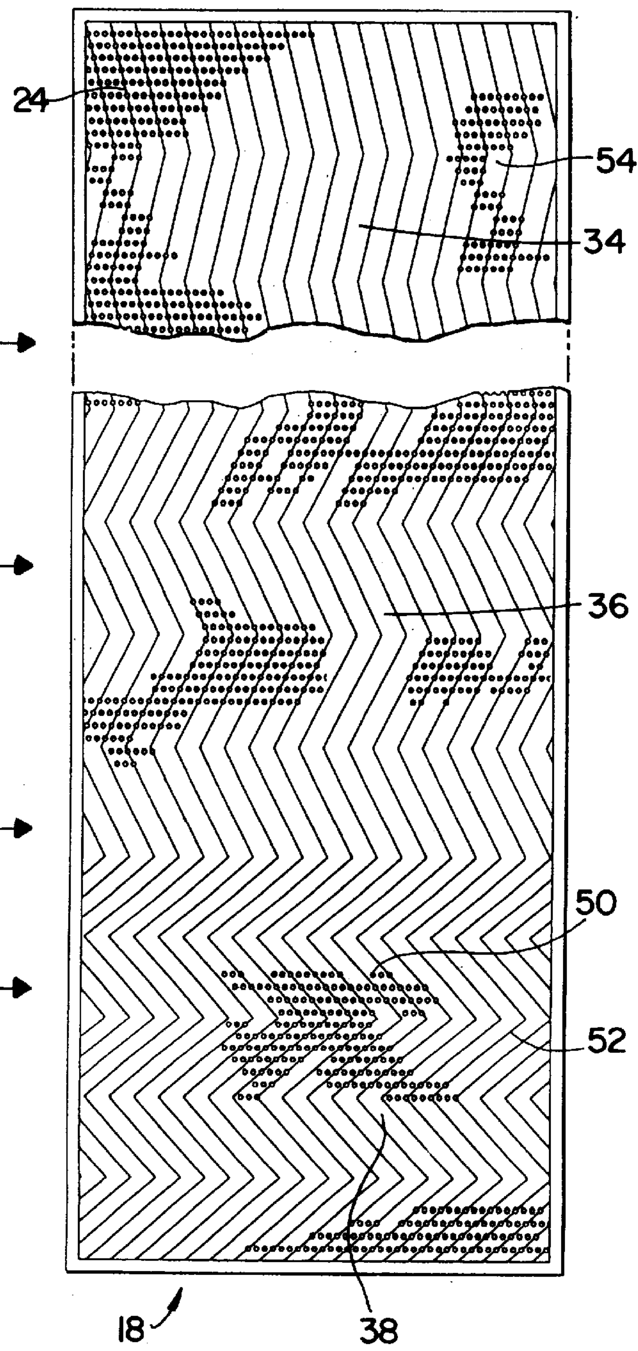
FIG. 2 is a schematic diagram of a corrugated plate for the liquid-liquid contacting of this invention.
Figure 3:
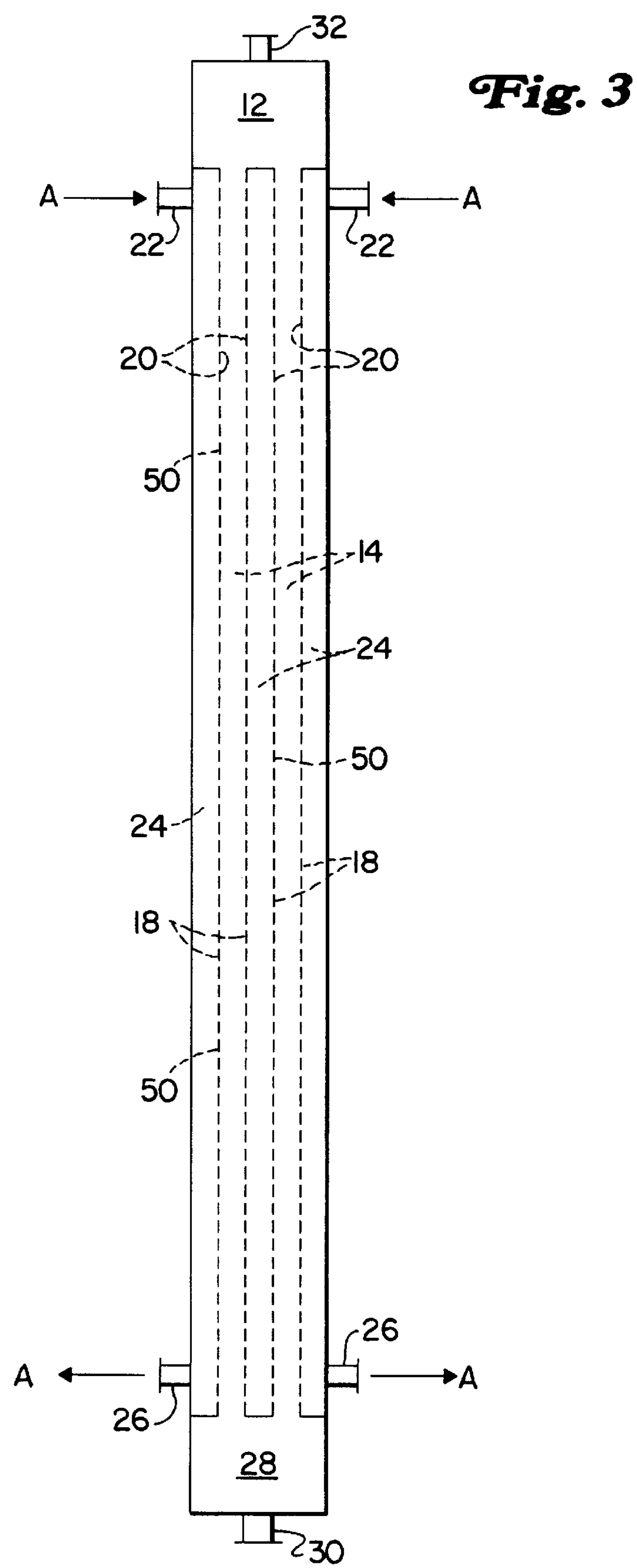
FIG. 3 is a schematic cross-section of a reactor arranged in accordance with this invention.

The general operation of the contactor of this invention may be more fully appreciated from the drawings. FIG. 1 shows a generalized flow arrangement of a reaction zone 10 that injects a fluid reactant into another stream of reactive fluid and that provides simultaneous cooling by indirect heat exchange. FIG. 2 schematically shows a typical corrugated plate 18 having corrugations with peaks 52, valley 54, and perforations 50. Plates 18 define distribution channels 24 and reaction channels 14 as more fully shown in FIG. 3. Distribution channels 24 also serve as heat exchange channels in this particular arrangement and are equally well described as such. One liquid, a reactive fluid designated by stream B, enters the nozzle 32 at top of the reaction zone 10. Manifold 12 distributes the reactive fluid to the reaction channels 14 as shown in FIGS. 1 and 3. As shown by FIG. 3 the tops of the distribution channels 24 are closed to provide a sealed space for the isolated transfer of the additional reactant/heat exchange fluid.

The reactant fluid, shown by stream A in FIG. 3, enters the top of distribution channels 24 in reactor 10 through nozzles 22 and flows down the distribution channels 24. A desired amount the reactant fluid permeates through perforations 50 in plates 18 and diffuses into the reactive fluid as it exits from sides 20 of plates 18. The reactive fluid and reactant/heat exchange fluid will usually flow cocurrently. However, reactive stream and the reactant/ heat exchange fluid may be introduced to the system for cocurrent flow as shown by stream A or cross-current flow as shown by stream C. The remaining volume of the reactant/heat exchange fluid exits the bottom of the distribution channels 24 through nozzles 26. After addition of any make-up fluid and heat exchange the heating or cooling, the reactant/heat exchange fluid returns for continued passage through channels 24 via nozzles 22 and 26. Suitable manifolding arrangements for distributing and collecting the reactant fluid in any type of flow direction are well known.

Unreacted reactive fluid and products drop from reaction channels 24 and collect in lower chamber 28 at the bottom of reactor 10. Nozzle 30 withdraws fluid B from chamber 28 and passes it on to any necessary separation facilities for recovery of products and recycle of reactants.

A typical corrugation pattern for a plate 18 as shown in FIG. 2 may be uniform throughout or may vary down the length of the plate as shown in FIG. 2. FIG. 2 shows the corrugation patterns in the idealized fashion with solid lines showing the peaks 52 for the ridges of the corrugations and centralized valley portions 54 between the ridges.

Suitable distribution, heat exchange and contacting plates for this invention will comprise any plates which are easily secured in the reaction section in a stable configuration that readily retains a corrugated or other surface arrangement. The plates may be formed into curves or other configurations, but flat plates are generally preferred for stacking purposes. Thin plates are ordinarily used and typically have a thickness of from 1–2 millimeters. The plates are typically composed of ferrous or non-ferrous alloys such as stainless steels. The general herring bone pattern on the faces of the opposing corrugated plates preferably extends in opposite directions such that the opposing plate faces may be placed in contact with each other to form the flow channels and provide structural support to the plate sections.

The corrugation pattern may be varied to achieve a variety of contacting and reaction effects. In addition to increased turbulence such effects include heat exchange control. For example, where rapid heat exchange is desired, the corrugations may extend substantially longitudinally with respect to the fluid flow as shown by the upper section of corrugations in FIG. 2. As less cooling is needed, the ridges of the corrugations can be made more transverse, as shown by middle section 36 and lower section 38 in FIG. 2, to the flow to impede the flow thereby increasing surface area and heat turbulence for enhanced heat exchange. The reduced vertical run and increased pitch for each section of corrugation also increases the turbulence of the flowing liquid a nd improves the diffusion of the reactant fluid.

The transverse component of the ridges may increase continually or in the stepwise fashion as shown in FIG. 2 by sections 34, 36, and 38. As shown by FIG. 2, the channels defined by the corrugations generally run in a generally vertical direction. Chevron type corrugation arrangements that extend in a substantially horizontal direction should be avoided to prevent concentration of the liquid at the bottom points of the corrugation intersections. The arrangement of vertically continuous flow paths as shown in FIG. 2 keeps the fluid stream dispersed and avoids localized concentration of the fluid. A number of corrugated plate shapes can b e used. Alternate pattern of corrugations are shown in FIG. 4 an d FIG. 5.

The degree of turbulence may also be controlled by varying the amplitude of the corrugations and the frequency of the corrugations, which are otherwise referred to as the pitch and the depth of the corrugations. Corrugations having a large pitch or low frequency and shallow depth or low amplitude will provide a low degree of turbulence. Increasing either or both of the frequency and amplitude will raise the degree the turbulence.

Figure 5:
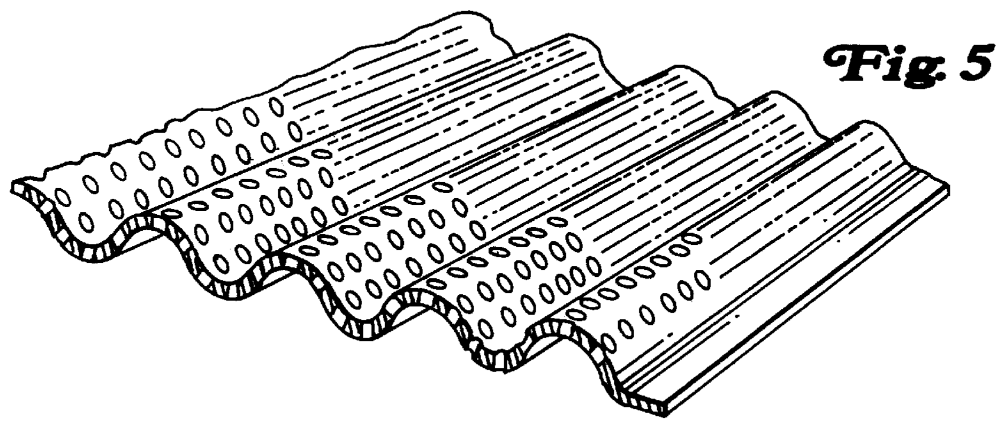
FIG. 5 is a schematic diagram of a perforated plate for the heat transfer channels of this invention.

The degree of heat transfer occurring over the heat transfer surface may be varied by including heat transfer plates between the permeable or perforated plates. In the case of corrugated plates, the provision of a separate heat transfer plate permits the pitch and number of corrugations on the heat transfer plate to vary independently with respect to the corrugations on the perforated plates Such an arrangement permits independent enhancement of heat transfer control over the length of the perforated plates without affecting the flow characteristic in the reaction channels. A heat exchange insert plate may be a flat plate with a turbulence inducing structure as shown in the U.S. Pat. No. 5,538,700, the contents of which are incorporated by reference herein, or an additional corrugated plate, preferably, containing perforations as shown by FIG. 2 and FIG. 5.

Figure 4:
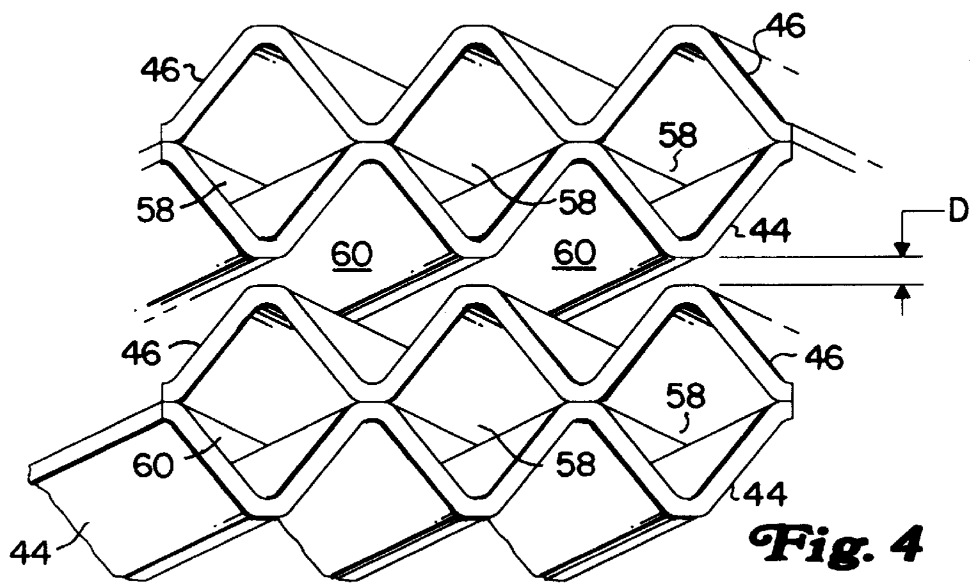
FIG. 4 is a three-dimensional view of a portion of the contacting and heat exchange channels of this invention shown with perforation omitted.

FIG. 4 depicts the tops of corrugated plates 44 and 46 into which corrugations are formed for defining distribution channels 58 and reaction channels 60. FIG. 4 shows the preferred arrangement where plates 44 and 46 are placed to contact adjacent corrugations in the distribution channels 58. The corrugations in the contacting channels 60 may be placed apart by distance D as shown in FIG. 4, but are preferably also placed in contact to avoid excessive deformation of the plates as a result of the relatively higher pressure in the distribution channels. The preferred arrangement of the corrugated plates with a herring bone pattern extending in different directions is more readily appreciated from FIG. 4. Corrugated plates 44 slope generally to the left as they extend downward while corrugated plates 46 extend transversely to the right as they slope downward.

The optional distance D will vary depending on the process conditions and the properties of the fluid. The distance D will typically be used merely to provide a larger volume in the flow channel for either the reactive or the reactant fluid. Spacing D may be maintained by use of occasional spacers that contact the points of the corrugations. Such spacers may consist of thin pins that extend over the entire vertical length of the contacting channels or thin bars that extend transversely across the contacting channels.

Figure 6:
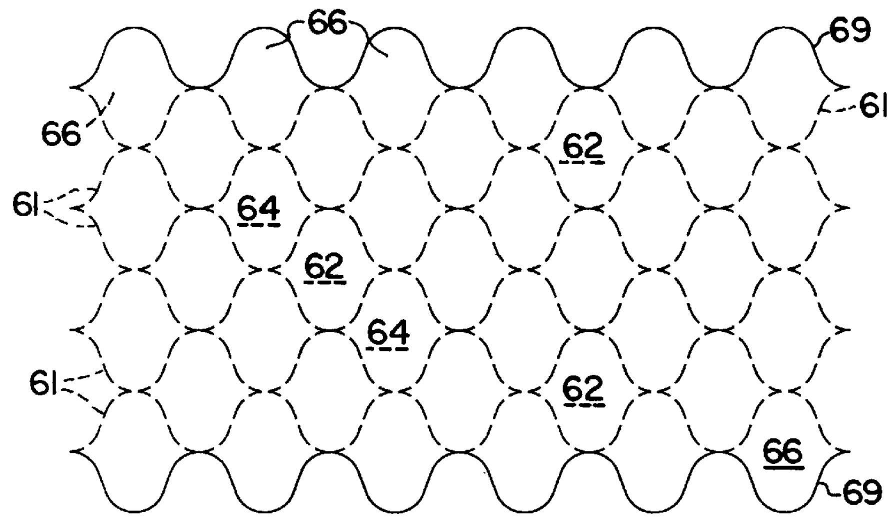
FIG. 6 is a schematic cross-section of channels arranged in accordance with this invention.

As more clearly illustrated in FIG. 6. all of the plates 61 defining the contacting channels 62 and the distribution channels 64 will preferably contain perforations except the outermost plates 69 defining the outermost channels 66. The outermost channels are preferably distribution and heat exchange channels so that all of the contacting channels receive heat exchange.

ILLUSTRATIVE EMBODIMENT

This invention can be used to operate an isothermal sulfonation process for the sulfonation of an alkyl benzene with sulfurtrioxide. In such an arrangement, an alkyl benzene stream comprising substituted benzene with alkyl groups and having from 12–14 carbon atoms passes in liquid phase through reaction channels as depicted in FIG. 1 and FIG. 3. A liquid stream of $SO_3$ flows parallel to the alkly benzene through the distribution channels to provide the sulfonating agent. Approximately 5% of the liquid $SO_3$ stream flows across the perforated plate separating the distribution and reaction channels and through fine perforations having an average diameter of about 0.02 in. that provide an opening area of about 5% of the total area of each plate. The temperature of the liquid $SO_3$ containing stream entering the distribution channels is about 20–25° C. The reactant stream passes through the reaction channel at a mass flow rate of about 500 Kg/Hr. The reactant stream as it passes over the plates is maintained at a temperature of about 50° C. by the excess $SO_3$ reactant that passes through the distribution/heat exchange channels. A once through passage of the hydrocarbon stream will produce an approximately 98% conversion.

What is claimed is:

1. A process for the reaction of a fluid stream by the controlled addition of a liquid reactant, said process comprising:

passing a first stream comprising a reactive fluid into a plurality of reaction channels defined by a first side of a plurality of stacked plates;

circulating a second stream comprising a reactant fluid through a plurality of distribution channels defined by a second side of said plurality of plates to provide indirect heat exchange with the reactive stream;

distributing a portion of said reactant fluid through permeable portions distributed over the surface of said plates to control the contact of said reactive fluid with the reactant fluid; and, recovering a reaction product from the reaction channels.

2. The process of claim 1 wherein the reaction is the sulfonation of a substrate with sulfur trioxide.

3. The process of claim 1 wherein said plates are corrugated and stacked to define vertically extended channels.

4. The process of claim 3 wherein said corrugations run at least partially transverse to the flow of the reactant stream.

5. The process of claim 4 wherein said corrugations extend diagonally across the surface of the plates in a plurality of rows and the vertical length of each diagonal is less than the vertical height of the plates.

6. The process of claim 4 wherein the corrugations of adjacent plates are in contact.

7. The process of claim 1 wherein said plates are perforated to provide said permeable sections.

8. The process of claim 1 wherein either the amplitude or the frequency of the corrugations is established to induce a desired degree of turbulence into said reactant stream as it passes down said corrugated surface.

9. The process of claim 1 wherein the volume of said reactant fluid passing into said reaction channels is less than 5% of said volume of said reactant fluid entering the distribution channels.

10. The process of claim 1 wherein the reactant fluid and the reactive fluid are maintained in liquid phase.

11. A process for the sulfonation of an organic liquid with a sulfonating liquid, said process comprising:

passing a reactive organic liquid through reaction channels defined by a first side of a plurality of vertically positioned corrugated plates that contain perforations;

circulating a reactant stream containing $SO_3$ through distribution channels defined by the second side of said vertical positioned plates to indirectly exchange heat with said organic liquid;

distributing a portion of the reactant stream through the perforations, and contacting the reactant stream with the organic liquid in said reaction channels; and, recovering a reaction product from said reaction channels.

12. The process of claim 11 wherein said organic liquid comprises toluene.

* * * * *